United States Patent [19]

Petruzzi

[11] Patent Number: 4,669,172
[45] Date of Patent: Jun. 2, 1987

[54] METHOD FOR FABRICATION OF FLEXIBLE SHAFT

[75] Inventor: Claude E. Petruzzi, Bronxville, N.Y.

[73] Assignee: Circon Corporation, Santa Barbara, Calif.

[21] Appl. No.: 799,299

[22] Filed: Nov. 20, 1985

Related U.S. Application Data

[63] Continuation of Ser. No. 465,852, Feb. 7, 1983, abandoned.

[51] Int. Cl.$^4$ ............................................. B23P 19/04
[52] U.S. Cl. ........................................ 29/456; 29/173; 29/558; 128/6; 138/131; 138/139
[58] Field of Search .......................... 29/456, 173, 558; 128/4, 6; 138/129, 131, 134, 139

[56] References Cited

U.S. PATENT DOCUMENTS

| 1,586,750 | 6/1926 | Joline | 138/131 X |
| 2,574,714 | 11/1951 | Smith | 29/173 X |
| 2,598,895 | 6/1952 | Dreyer | 138/139 X |
| 3,788,304 | 1/1974 | Takahashi | 128/6 |

Primary Examiner—Charlie T. Moon
Attorney, Agent, or Firm—Perman & Green

[57] ABSTRACT

Disclosed is a method for the fabrication of a flexible shaft comprising a spiral cut member having an essentially uniform inside diameter and a tapered linear profile coextensive with at least a portion of the spiral of said member. This flexible shaft is fabricated initially by progressively removing a portion of the exterior wall along a predetermined segment of a relatively rigid tube thereby forming a tapered profile along such segment. A series of cuts are thereafter made in the wall of the tapered segment of the tube resulting in a progressive and transition free increase in flexibility along itslongitudinal dimension; that portion of the tapered segment having the thinner wall being increasingly more flexible than that portion of the tapered segment having a comparatively thicker wall.

9 Claims, 4 Drawing Figures

METHOD FOR FABRICATION OF FLEXIBLE SHAFT

This is a continuation of co-pending application Ser. No. 465,852 filed on 2/7/83, now abandoned.

BACKGROUND OF THE INVENTION

1. Field of the Invention

This invention relates to a method of manufacture and the manufactured article. More specifically, this invention concerns itself with an improved technique for the fabrication of flexible shafts for endoscopic instruments and the products which result from this improved technique.

2. Description of the Prior Art

The advent of flexible endoscopes has made possible the invasive, non-surgical examination of the gastrointestinal tract. As is readily appreciated, the more compliant and flexible the shaft of these instruments, the less discomfort experienced by the patient during examination by the physician. The flexible shaft of such instruments is typically formed by spiral winding a ribbon of metal in the form of a helix. The helix can thereafter be soldered on either end to a tubular element which forms the point of attachment to the control head of the instrument and to the objective assembly. In order to increase torsional stability of the helix, the ribbon spiral is further enveloped in a mesh-like material which in turn is further enclosed by a flexible plastic sheath. Typically, the interior of shaft will also include various guides or other means for segregating the control wires, optical bundles and instrument channels which course through it from the control head to the distal end of the instrument. U.S. Pat. No. 2,243,922 (to Wappler) is illustrative of the type of instrument described hereinabove.

Various fabrication techniques are known to effect the resiliency of the flexible shaft suitable for use in endoscopic instruments. These techniques include varying the thickness and/or width of the ribbon used in the fabrication of the spiral tube; selection of metals of varying hardness for such ribbon and the construction of the flexible tube by physically or mechanically joining together two spirals of dissimilar flexibility. Where this latter practice is followed, there is generally an abrupt transition in flexibility from one segment of the flexible shaft to another. Not only is this undesirable, but dramatically increases the cost of fabrication of the flexible element and the potential for failure at the junction where such similar elements are joined together.

Another technique commonly employed in the construction of flexible shafts for endoscopes is described in U.S. Pat. No. 3,799,151 (to Fukaumi et.at). In FIG. 2 of the '151 patent, a deflectable tube for an endoscope is constructed by the joining together of individually hinged segments wherein the hinged axis between each successive segment is perpendicular to the other when the tube in in the normally extended position. U.S. Pat. No. 4,108,211 (to Tanaka) also shows a deflectable tube structure formed of segmented vertebrae whose deflections are controlled by wires. Another expedient for imparting flexibility to a tubular member involves the executing of a predetermined number of cuts or slots in the tube wall, see e.g. FIG. 7 of U.S. Pat. No. 4,134,405 (to Smit).

All the expedients described heretofor in the fabrication of flexible shafts for endoscopic instruments, and the like, suffer from one more of the following shortcomings which include: (a) complexity of manufacture, (b) inability to readily form a shaft of unitary structure having either uniform or variable flexibility, and/or (c) inability to readily form a shaft of unitary structure having progressively variable flexibility without an abrupt transition between such areas of dissimilar flexibility.

OBJECTS OF THE INVENTION

It is, therefore, the object of this invention to remedy the above, as well as, related deficiencies on the prior art.

More specifically, it is the principal object of this invention to provide a method for the fabrication of a unitary flexible shaft from a tubular member wherein the flexible segment thereof has varying degrees of flexibility.

It is also an object of this invention to provide a method for the fabrication of a unitary flexible shaft of varying flexibility that is essentially free of abrupt transitional areas along the flexible segment thereof.

It is a further object of this invention to provide a method for the fabrication of a unitary flexible shaft from a tubular member by convenient and readily available machining techniques.

It is another object of this invention to provide a method for the fabrication of a unitary flexible shaft from a tubular member of essentially uniform wall thickness.

It is still yet another object of this invention to provide a method for the fabrication of a unitary flexible shaft from a tubular member having an essentially uniform inside diameter.

Additional objects of this invention include the provision of flexible tubular members of unitary construction and their utilization in an endoscopic environment.

SUMMARY OF THE INVENTION

The above and related objects are achieved by providing a method for producing a flexible shaft suitible for use in endoscopic instruments, by initially progressively removing a portion of the exterior wall of a tubular member over a predetermined linear segment thereof resulting in the tapering of a profile of the tubular member along the length of such segment. Thereafter, a portion of the wall of this tapered segment is selectively removed by executing a pattern of cuts through said wall whereby the combined effect of the tapering and the cutting of the wall of the tubular member along this segment results in a progressive and a transition free increase in flexibility along the length of that segment. The degree of flexibility along the segment is in proportion to the relative thickness of the wall with that portion of the segment having the thinner wall being more flexible than that portion of the segment having a comparatively thicker wall.

DETAILED DESCRIPTION OF THE INVENTION INCLUDING PREFERRED EMBODIMENTS

Figure 1:
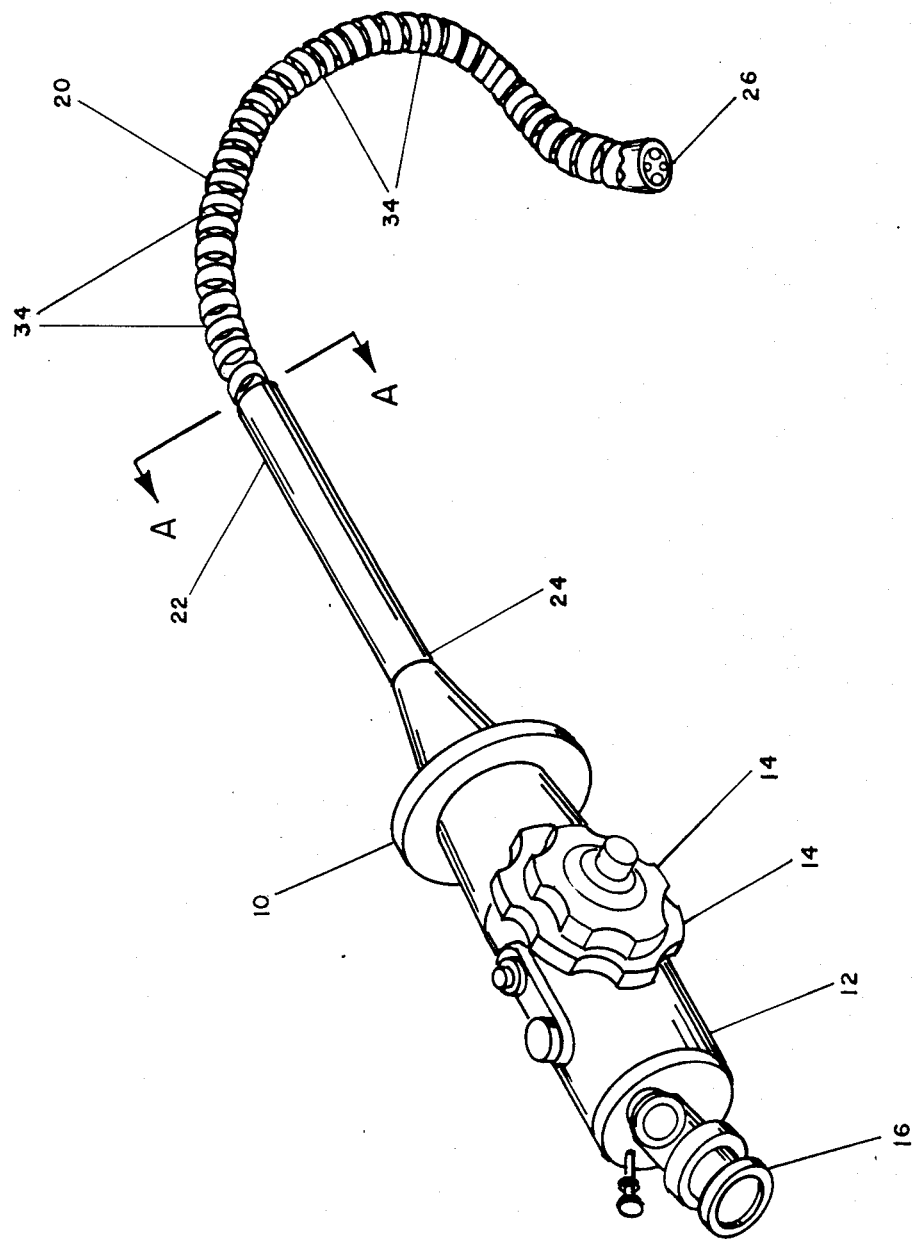
FIG. 1 is a perspective view in partial cutaway, of an endoscopic instrument incorporating the flexible shaft prepared in accordance with the method of this invention.

In FIG. 1 is shown an endoscopic instrument 10 having at its proximal end a control head 12 with a deflection control wheels 14 and 14' and viewing optics 16. This control head is connected through flexible shaft 18 to an objective element 26 located at the opposite or distal end of the flexible shaft. As is common in instruments of this type, the flexible shaft houses a plurality of channels and fiber optic elements necessary in the operation and manipulation of the instrument. One such fiber optic bundle 30 connects the optics located in the control head to the objective at the distal end of the flexible shaft. In a like manner, a second fiber optic bundle 32 connects a light source (not shown), which is generally independent of the instrument, through an umbillicus or fitting on the control head, to a second lens system at the distal end of the flexible shaft. In operation of the instrument, the physician initially inserts the flexible end thereof into the GI tract of the patient, and manipulates the objective tip of the shaft through the control wheel on the control head. Movement of the control wheel effects omnidirectional movement of the shaft through a series of cables 75, 76, 77 and 78 which are connected from the control wheel to the distal end of the flexible shaft. Movement of one or both elements of the control wheel can be performed sequentially or simultaneously and the resulting deflection will be a product of both such movements.

Figure 2:
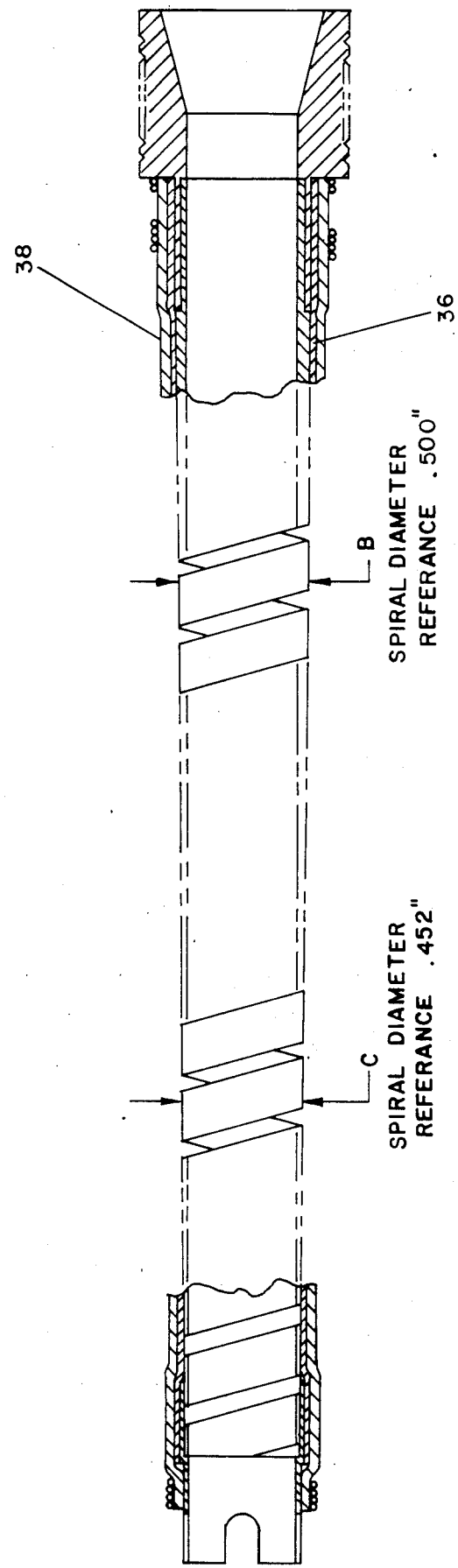
FIG. 2 is an enlarged cutaway view of the flexible shaft of the endoscopic instrument illustrated in FIG. 1.
Figure 3:
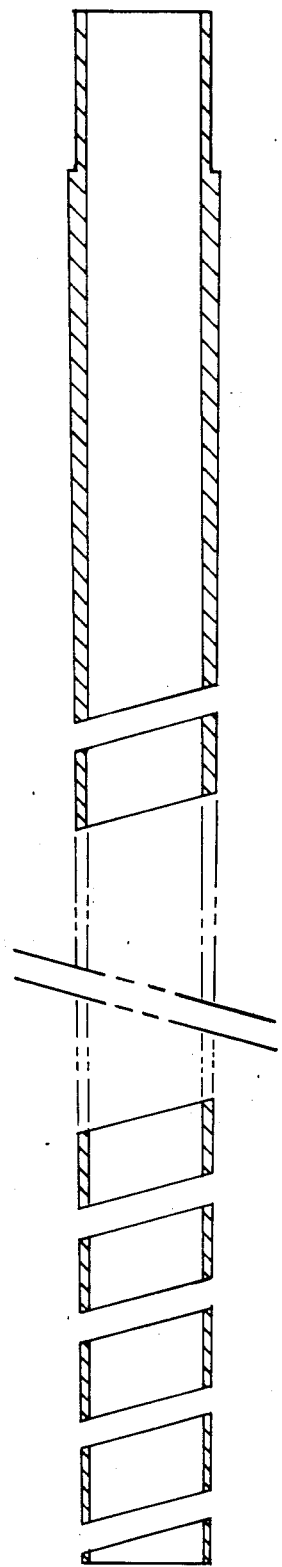
FIG. 3 is a longitudinally section through the spiral cut tubular element of the flexible shaft of FIG. 2.

Examination of the flexible shaft in greater detail in FIG. 2 illustrates the unique features of this element. Unlike the spiral wound flexible members heretofor described in the prior art, the shaft illustrated in FIG. 2 is formed by initially machining a tubular member so as to taper the tube a predetermined amount followed by the execution of a spiral cut along the tube, including that portion which has been tapered. As is evident from comparison of the cross sectional area at line B—B with a cross section of the tube at line C—C, the outer wall thickness of the tube has been reduced by approximately ten percent (10%) while no corresponding change has been effected to the interior thereof. Thus, the resistance of the tube to deflection is dramatically increased prior to removal of a portion of the tubular wall through the execution of a pattern of cuts in said wall.

Figure 4:
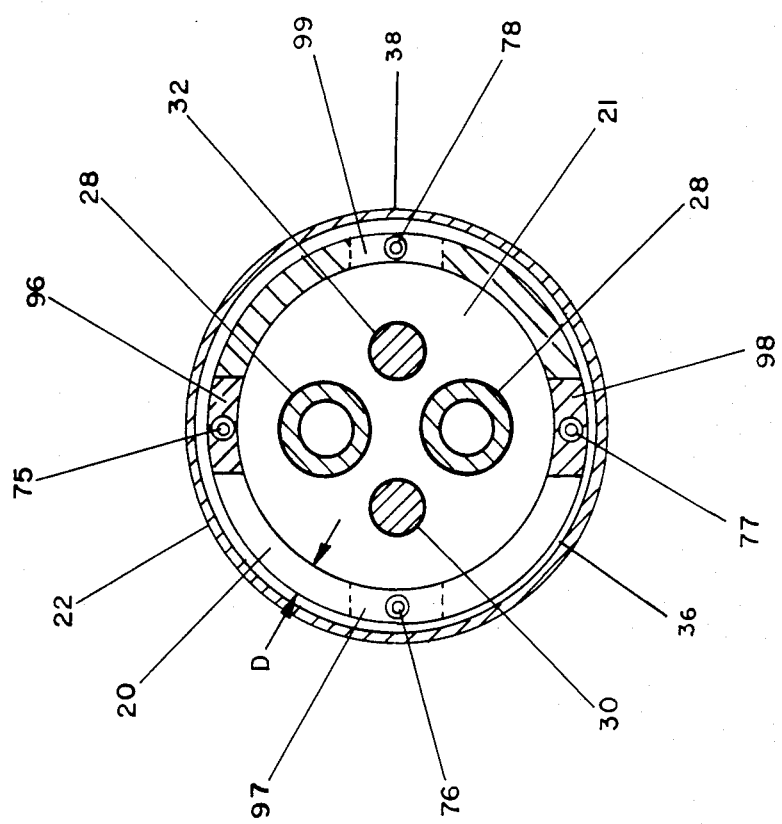
FIG. 4 is a cross-section through FIG. 1 at A—A.

In the particular embodiment of the method, the results of which are illustrated in FIG. 2, the tubular member was turned on a lathe while a spiral pattern was cut along its longitudinal dimension. As can be clearly seen in the Figures, the spiral cut and the taper both extend from adjacent the objective 26 at one end of the tubular member inwardly for at least the majority of the length of the tubular member. The spiral angle can be at any preselected pitch and need not be constant over the entire length of the tube. Moreover, the width of the cut can also be varied. Both the change in angle of the helix and in the width of the cut will also increase the flexibility of the shaft even further. In the preferred embodiment of this invention the helical angle is approximately fourteen to fifteen degrees (14°–15°), the width of the cut approximately 0.10 inches and the width of the helical band approximately 0.25 inches. In the cutaway illustrated in FIG. 2, the tapered helical member is enveloped within woven mesh 36 to impart torsional stability. The entire assembly is thereafter enclosed in plastic sheath 38. At the proximal end of the shaft a bayonet fitting is affixed to one inflexible end of the shaft for mating to the control head; whereas, a threaded fitting is affixed to the distal end for connection to the objective. The interior of the shaft is further modified with a series of retainers 96, 97, 98 and 99 as illustrated in FIG. 4 which serve as guides for the control cables which course through the shaft from the control head to the distal end of the flexible shaft. In addition, one or more channels 28 and 28 are provided within the shaft for fiber optic bundles, manipulative instruments and a water channel.

While the foregoing invention has been described with reference to the fabrication of flexible members for endoscopic instruments, it is clearly anticipated that the novel technique described hereinabove can be applied to various other applications where the fabrication of crimp resistant conduit is desired, whether that conduit be metalic, or fabricated from a natural or synthetic polymeric resin.

What is claimed is:

1. In a method for producing a flexible shaft suitable for use in endoscopic instruments, the improvement comprising:
   a. progressively removing a portion of the exterior wall of a tubular member having an essentially uniform inside diameter over a predetermined linear segment of a majority of the length of said member, thereby tapering the profile of said member along the length of said segment;
   b. further removing a portion of the wall of the tapered segment of said tubular member by executing a spiral shaped pattern of cuts through said wall, the combined effect of the tapering and cutting of said segment resulting in a progressive and transition free increase in flexibility of said segment along the longitudinal dimension thereof, with that portion of the tapered segment having the thinner wall being increasingly more flexible than that portion of the wall having a comparatively thicker wall; and surrounding the spiral element of the shaft in a sheath to impart torsional stability to the shaft.

2. The method of claim 1, wherein the pattern of cuts executed in said tubular member converts said tube to a spiral cut flexible shaft.

3. The method of claim 2, wherein the pitch of the spiral is essentially constant over the length of the tapered segment of said shaft.

4. The method of claim 2, wherein the pitch of the spiral is variable over the length of the tapered segment of said shaft.

5. The method of claim 2, wherein the width of the spiral cut is variable over the length of the tapered segment of said shaft.

6. The method of claim 1, wherein the tubular member is fabricated from a metal.

7. The method of claim 1, wherein the tubular member is fabricated from a natural or synthetic polymeric resin.

8. In a method for producing a flexible shaft suitable for use in endoscopic instruments, the improvement comprising:
   a. progressively removing a portion of the exterior wall of a tubular member having an essentially uniform inside diameter over a predetermined linear segment of said member, thereby tapering the profile of said member along the length of said segment from adjacent one end of the tubular member inwardly for at least the majority of the length of the tubular member; and b. further removing a portion of the wall of the tapered segment of said tubular member by executing a spiral shaped pattern of cuts through said wall, the spiral shaped pattern of cuts extending from adjacent one end of the tubular member inwardly for at least the majority of the length of the tubular member, the combined effect of the tapering and cutting of said segment resulting in a progressive and transition free increase in flexibility of said segment along the longitudinal dimension thereof, with that portion of the tapered segment having the thinner wall being increasingly more flexible than that portion of the wall having a comparatively thicker wall.

9. The method of claim 8 comprising the additional step of surrounding the spiral element of the shaft in a sheath to impart torsional stability to the shaft.

* * * * *